（12) United States Patent
Moon

(10) Patent No.: US 10,716,961 B2
(45) Date of Patent: Jul. 21, 2020

(54) HEAD BAND MEMBER FOR WEARING RESPIRATOR MASK AND HEAD CRADLE INCLUDING SAME

(71) Applicant: 3M INNOVATIVE PROPERTIES COMPANY, St. Paul, MN (US)

(72) Inventor: Jungchul Moon, Hwaseong-si (KR)

(73) Assignee: 3M Innovative Properties Company, St. Paul, MN (US)

( * ) Notice: Subject to any disclaimer, the term of this patent is extended or adjusted under 35 U.S.C. 154(b) by 268 days.

(21) Appl. No.: 15/752,931

(22) PCT Filed: Aug. 18, 2016

(86) PCT No.: PCT/US2016/047454
§ 371 (c)(1),
(2) Date: Feb. 15, 2018

(87) PCT Pub. No.: WO2017/031263
PCT Pub. Date: Feb. 23, 2017

(65) Prior Publication Data
US 2018/0236276 A1 Aug. 23, 2018

(30) Foreign Application Priority Data
Aug. 20, 2015 (KR) ........................ 10-2015-0117271

(51) Int. Cl.
*A62B 18/08* (2006.01)
*A41D 13/11* (2006.01)
(Continued)

(52) U.S. Cl.
CPC ........ *A62B 18/084* (2013.01); *A41D 13/1161* (2013.01); *A44B 11/006* (2013.01); *A61M 16/0683* (2013.01); *A62B 18/025* (2013.01)

(58) Field of Classification Search
CPC ....... A62B 18/00; A62B 18/02; A62B 18/025; A62B 18/084; A61M 16/0488;
(Continued)

(56) References Cited

U.S. PATENT DOCUMENTS 1,224,039 A * 4/1917 Synohubyk ....... A61M 16/0683
128/207.11
3,040,741 A * 6/1962 Carolan ............... A62B 18/084
128/206.27
(Continued)

FOREIGN PATENT DOCUMENTS

JP 07034706 U 6/1995
KR 2003-38228 U 1/2004
(Continued)

OTHER PUBLICATIONS

International Search Report for PCT International Application No. PCT/US2016/047454, dated Nov. 8, 2016, 5 pages.

*Primary Examiner* — Joseph D. Boecker

(57) ABSTRACT

There is provided a head band member (100) for wearing a respirator mask (1) and a head cradle (10) including the same. The head band member (100) includes a supporting member (130) extending in a direction; a first coupling portion (110) formed at one end portion of the supporting member (130), and including an insertion hole (116) formed to pass therethrough; a second coupling portion (120) formed at another end portion of the supporting member (130); and a strap connection portion (140) formed at an end portion of the first coupling portion (110) or the second coupling portion (120), and connected with a strap (30), wherein at least a part of the second coupling portion (120) being inserted into the insertion hole (116) of the first coupling portion (110) and thereby the first coupling portion (110) and the second coupling portion (120) are provided to be coupled to each other, and the head band member (100) is connected to a mask body (20) of a respirator mask (1) through the strap (30).

20 Claims, 9 Drawing Sheets

(51) Int. Cl.
*A61M 16/06* (2006.01)
*A44B 11/00* (2006.01)
*A62B 18/02* (2006.01)

(58) Field of Classification Search
CPC .............. A61M 16/06; A61M 16/0683; A41D 13/1161; A44B 11/006; A42B 3/288; B63C 2011/128
See application file for complete search history.

(56) References Cited

U.S. PATENT DOCUMENTS

| | | | |
|---|---|---|---|
| 3,234,939 A * | 2/1966 | Morton, Jr. | A62B 18/084 128/206.27 |
| 5,653,228 A * | 8/1997 | Byrd | A61M 16/0488 128/207.11 |
| 6,119,693 A | 9/2000 | Kwok | |
| 6,907,882 B2 | 6/2005 | Ging | |
| D532,511 S | 11/2006 | Amarasinghe | |
| 2004/0221432 A1 | 11/2004 | Nezu | |
| 2011/0220115 A1* | 9/2011 | Castiglione | A62B 18/084 128/206.27 |
| 2013/0092174 A1* | 4/2013 | Jackman | A61M 16/0683 128/207.18 |
| 2014/0216463 A1* | 8/2014 | Cowell | A62B 18/084 128/207.11 |
| 2018/0235322 A1* | 8/2018 | Moon | A44B 11/006 |

FOREIGN PATENT DOCUMENTS

| | | | |
|---|---|---|---|
| KR | 2013-0013450 | 2/2013 | |
| KR | 1020130049180 | 5/2013 | |
| WO | WO 2011-112401 | 9/2011 | |
| WO | WO 2012-104756 | 8/2012 | |
| WO | WO 2017-031262 | 2/2017 | |
| WO | WO-2018134767 A1 * | 7/2018 | ............... A62B 9/04 |

* cited by examiner (B-B)

HEAD BAND MEMBER FOR WEARING RESPIRATOR MASK AND HEAD CRADLE INCLUDING SAME

CROSS REFERENCE TO RELATED APPLICATIONS

This application is a national stage filing under 35 U.S.C. 371 of PCT/US2017/031263 filed Aug. 18, 2016, which claims the benefit of Korean Application No. 10-2015-0117271, filed Aug. 20, 2015, the disclosure of which is incorporated by reference in its/their entirety herein.

The present disclosure relates to a head band member for wearing a respirator mask and a head cradle including the same.

In general, respirators, which are protective devices to prevent wearers from absorbing contaminants from a surrounding environment, are in tight contact with and are worn on noses and mouths of wearers to separate contaminated surrounding air from the inside of masks where clean air is. At this time, the mask can be used for filtering air which passes therethrough. This type of respirator is used for many industries including construction, manufacturing, automotive painting and repairing, pharmaceutical production, surgery and the like.

Such a respirator is connected to a head cradle which is provided so that a strap connected to both ends of the mask is worn on the head of the wearer, and the mask can be maintained in a close contact state with the face of the wearer by the head cradle.

An example of the conventional head cradle used for wearing the respirator is disclosed in Korean Unexamined Patent Application Publication No. 10-2013-0049180 ("Patent Document 1").

A head cradle disclosed in the Patent Document 1 includes first and second lateral extension members, and has a structure that the first and second lateral extension members are fit on the head of a wearer and supported when a wearer wears a respirator. At this time, since the first and second lateral extension members are formed to be pivotable with respect to each other on a pivot point, when a wearer puts a mask around the neck, the first and second lateral extension members can be changed into a folded state by pivoting in a direction to approach each other. Thus, the mask body can be positioned at a storing position where a face is not covered when seen from in front of the breast of the wearer.

SUMMARY

However, the conventional head cradle as described above has the following problems. Since a first lateral extension member and a second lateral extension member forming a head cradle have different shapes from each other, they are manufactured through different processes. Thus, there is a problem that the manufacturing process of the head cradle is not simple.

In addition, when the first lateral extension member and the second lateral extension member are pivoted with respect to each other and worn on a head, comparative positions of the two members are fixed by a latching mechanism, however, the second lateral extension member is only prevented from straying into an outside of a latch of the first lateral extension member by the latching mechanism, and there is no way to prevent the second lateral extension member from moving toward an inside of the latch. There are also problems in that the two members cannot be completely fixed to each other, such that a rattling feeling can be conveyed to a wearer.

In addition, when the second lateral extension member is coupled to the latch, when the wearer continuously pushes the second lateral extension member into the inside of the latch in a state in which the second lateral extension member stops at an outside of the latch, the second lateral extension member is suddenly inserted into and coupled to the inside of the latch, and then, there is a problem that a click feeling is not smooth when the head cradle is worn and also folded to put the head cradle around a neck.

Embodiments of the present disclosure, which are provided to solve the aforementioned problems, provide a head band member and a head cradle including the same that may have a simple manufacturing process; may convey a feeling in which a mask is reliably fixed on the head of a wearer when the mask is worn on a face; and may convey a smooth click feeling when the mask is folded or unfolded to be worn on a head or be put around the neck.

One aspect of the present disclosure provides a head band member including a supporting member extending in a direction; a first coupling portion formed at one end portion of the supporting member, and including an insertion hole formed to pass therethrough; a second coupling portion formed at the other end portion of the supporting member; and a strap connection portion formed at an end portion of the first coupling portion or the second coupling portion, and connected with a strap, wherein at least a part of the second coupling portion being inserted into the insertion hole of the first coupling portion and thereby the first coupling portion and the second coupling portion are provided to be coupled to each other, and the head band member is connected to a mask body of a respirator mask through the strap, and a wearing state of the respirator mask is maintained.

According to embodiments of the present disclosure, there is an effect that the embodiments have a simple manufacturing process, convey a feeling in which a mask is reliably fixed on the head of a wearer when the mask is worn on a face, and convey a smooth click feeling when the mask is folded or unfolded to be worn on a head or be put around the neck.

In addition, there is an effect that even when once coupled to each other and used for a long time, the lifetime of products is increased compared to a conventional one, because of not being separated easily.

DISCLOSURE

Hereinafter, exemplary embodiments for realizing the spirit of the present invention will be described in detail with reference to the drawings. Here, for convenience of explanation, the drawings are not drawn to scale. Also, in the description of the present invention, when it is considered that the specific description of the related and noticed functions or structures may obscure the gist of the present invention, the specific description will be omitted.

Figure 1:
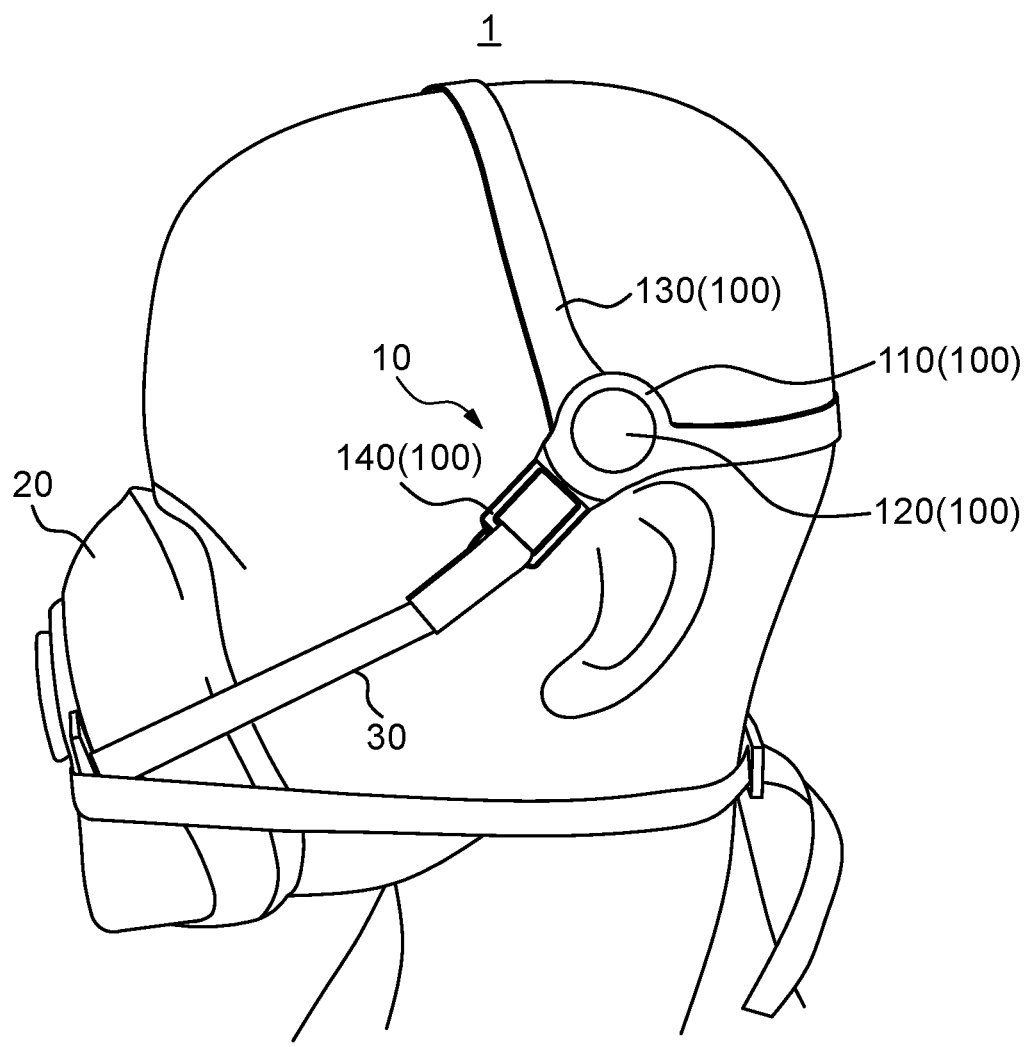
FIG. 1 is a view illustrating a state in which a head cradle according to a first embodiment of the present invention is worn on the head of a wearer.
Figure 2:
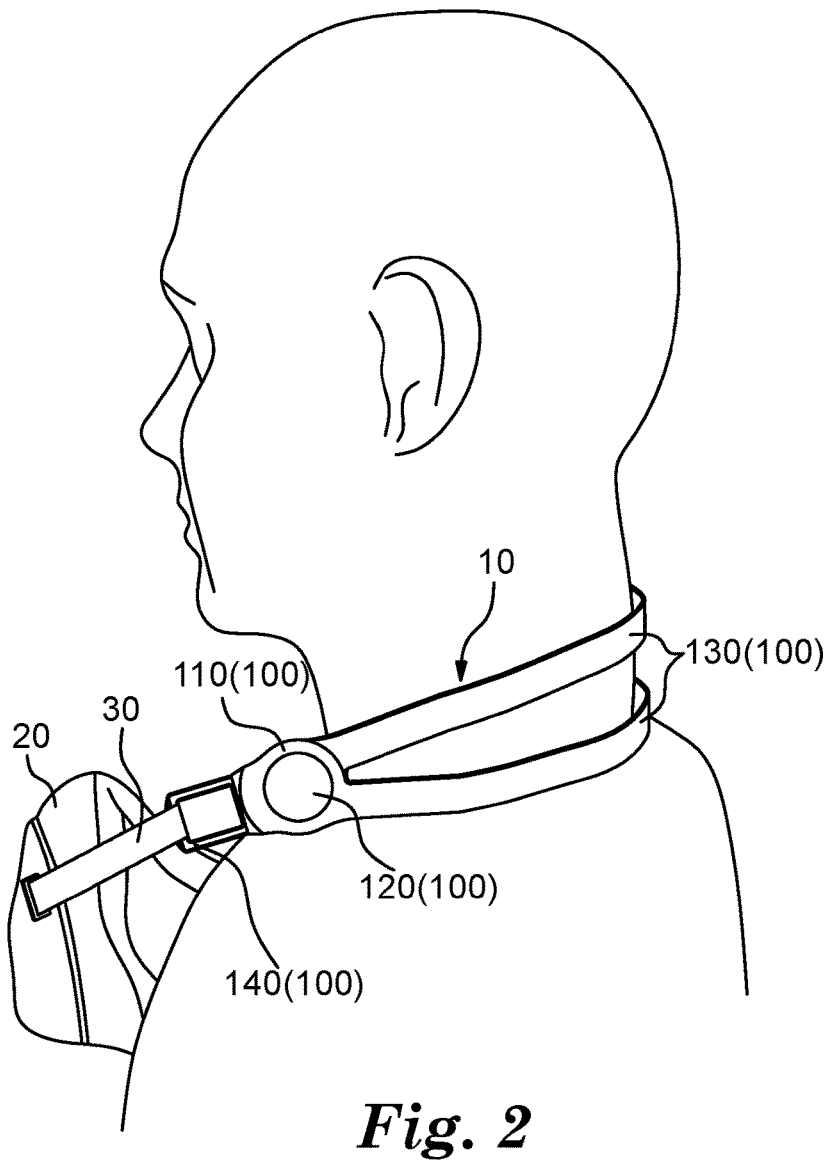
FIG. 2 is a view illustrating a state in which the head cradle in FIG. 1 is folded and put around the neck of a wearer.
Figure 3:
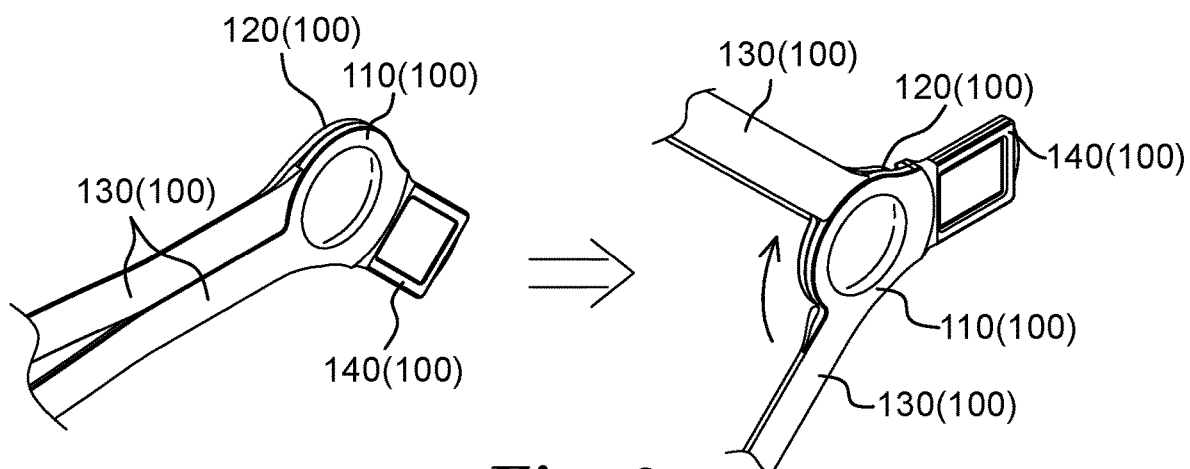
FIG. 3 is a view illustrating shapes in which the head cradle in FIG. 1 is folded and unfolded.

FIG. 1 is a view illustrating a state in which a head cradle according to a first embodiment of the present disclosure is worn on the head of a wearer, FIG. 2 is a view illustrating a state in which the head cradle in FIG. 1 is folded and put around the neck of a wearer, and FIG. 3 is a view illustrating shapes in which the head cradle in FIG. 1 is folded and unfolded.

Referring to FIGS. 1 to 3, a head cradle 10 according to one embodiment of the present disclosure may be used for wearing a respirator mask 1 which is in close contact with the nose and the mouth of a wearer and protects the wearer from absorbing contaminants in a surrounding environment. The respirator mask 1 may include a mask body 20 which is in contact with the face of the wearer and blocks foreign materials from flowing into the respirator.

The mask body 20 may be formed to cover the mouth and nose of a wearer, include a protruded portion so that a wearer does not feel discomfort, include both sides connected to straps 30, and be connected to the head cradle 10 by the straps 30.

In addition, the mask body 20 may include a filter configured to filter air that a wearer inhales. For example, the mask body 20 may include a filtering structure including one or more filtering layers, and a supporting structure to support the filtering structure and maintain a shape. At this time, the filtering structure may be formed in a sheet type, and formed in a various shapes and structures.

In addition, the filtering structure may include a fluid permeable surface area through which air may pass when a wearer inhales or exhales.

In addition, the filtering structure may be a particle trapping filter or a gas and vapor filter. According to a case, the mask body 20 may further include an exhalation valve (not shown) which is connected to the filtering structure and may quickly remove air, that a wearer exhales, from an inside of the mask, and the exhalation valve may be formed at a middle portion of the mask body 20.

The strap 30 may include one end connected to a side portion of the mask body 20, and the other end connected to the head cradle 10. In addition, the strap 30 may have an elasticity so that a total length is increased 2 fold when an external force is applied, and may be restored to a relaxed state when the external force is removed.

The straps 30 of both sides of the mask body 20 may extend to a certain length, and be connected to the head cradle 10 on both sides of the head of a wearer, at this time, the strap 30 may have a tension due to a restoring force of the elastic strap 30, and the mask body 20 may be in close contact with the face of a wearer due to the tension of the strap 30.

For example, the strap 30 may have a length of about 25 to 60 cm, a width of 5 to 10 mm, and a thickness of 0.9 to 1.5 mm.

In addition, the strap 30 may be manufactured of various materials, for instance, a thermosetting rubber, a thermoplastic elastomer, a combination of braided or knitted yarn and rubber, inelastic braided elements or the like.

Meanwhile, the head cradle 10 may be formed of two head band members 100. Referring to FIG. 3, the two head band members 100 are coupled to each other through a first coupling portion 110 and a second coupling portion 120 formed at end portions, and are pivotable with respect to the first and second coupling portions 110 and 120 at a predetermined angle and are able to be unfolded or foldable.

Thus, the two head band members 100 may be manufactured in a manner in which the two head band members 100 forming the head cradle 10 may be worn on the head of a wearer in an unfolded state, and the respirator mask 1 may be fixed to the face of the wearer, and when the wearer releases the head cradle 10 from a worn state and takes respirator mask 1 off and puts it around the neck, the two head band members 100 may be folded and be easily put around the neck.

Figure 4:
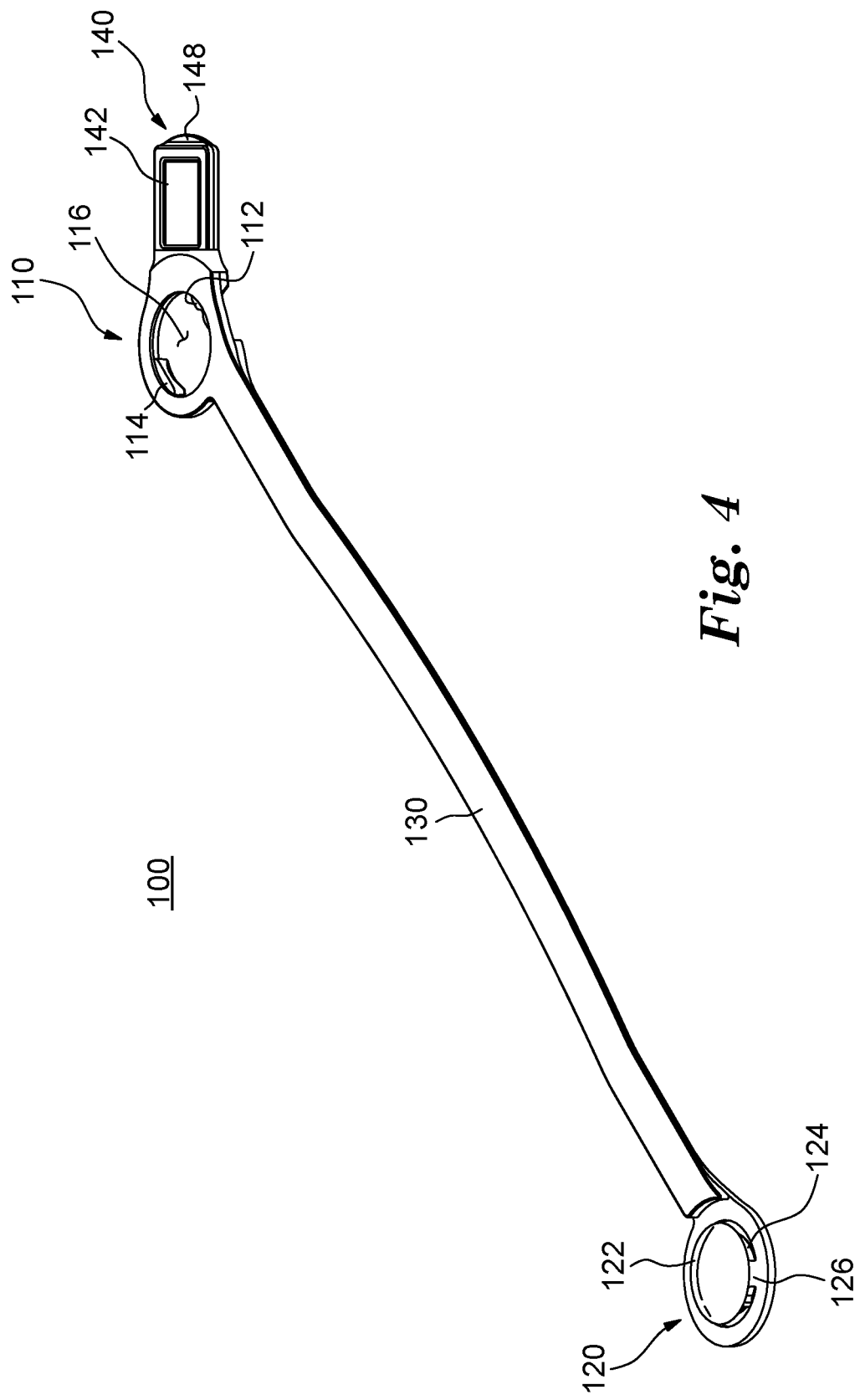
FIG. 4 is a perspective view of the head band member in FIG. 1.

A specific structure of the head band member 100 will be described in accordance with FIGS. 4 to 6. FIG. 4 is a perspective view of the head band member in FIG. 1, FIG. 5 is a view illustrating the first coupling portion of the head band member in FIG. 1, and FIG. 6 is a view illustrating the second coupling portion of the head band member in FIG. 1.

Figure 5:
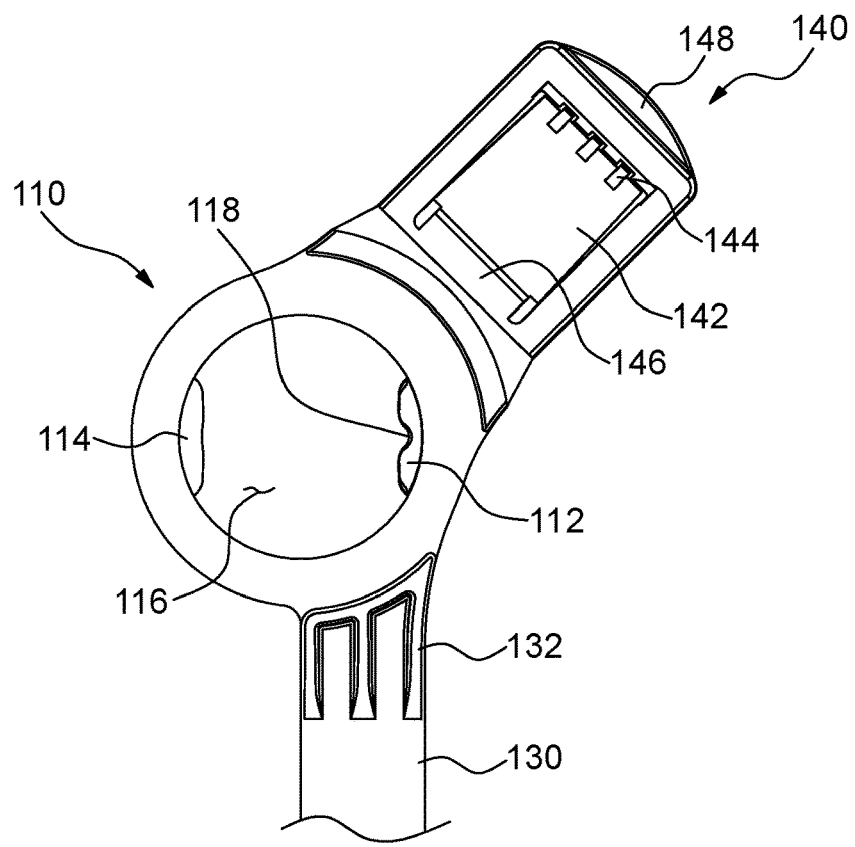
FIG. 5 is a view illustrating the first coupling portion of the head band member in FIG. 1.
Figure 6:
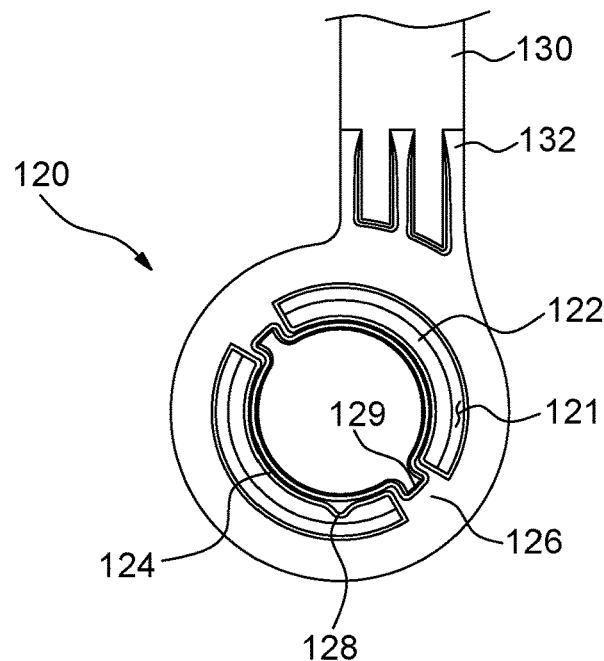
FIG. 6 is a view illustrating the second coupling portion of the head band member in FIG. 1.

Referring to FIGS. 4 to 6, the head band member 100 may include a supporting member 130 extending in a direction, the first coupling portion 110 formed at one end portion of the supporting member 130, the second coupling portion 120 formed at the other end portion of the supporting member 130, and a strap connection portion 140 formed at the end portion of the first coupling portion 110 or the second coupling portion 120 and connected to the strap 30 (not shown).

In addition, the head band member 100 may be formed of a flexible material, as an example, may be formed of a polymer based plastic material having a flexibility, and have a flat shape having two sides opposite to each other.

Specifically, the first coupling portion 110 may include an insertion hole 116 formed to pass from one side to the other side, and a click protrusion 112 and a stopper 114 formed to protrude from an inner circumferential surface of the insertion hole 116. In addition, the click protrusion 112 and the stopper 114 may protrude from both ends of the insertion hole 116 in a diameter direction. However, this is merely an example, the concept of the present disclosure does not limit the positions at which the stopper 114 and the insertion hole 116 are formed.

A coupling groove 118 is recessively formed in a surface of the click protrusion 112 in a direction of a diameter of the insertion hole 116. The coupling groove 118 may have a shape capable of accommodating a coupling protrusion 128 protrusively formed on a flexible ring 124 of the second coupling portion 120.

In addition, the click protrusion 112 and the stopper 114 may each have one inclined surface having a thickness decreasing toward a center of the insertion hole 116. The inclined surfaces formed on the click protrusion 112 and the stopper 114 may enable a cap 122 of the second coupling portion 120 to smoothly enter the insertion hole 116 of the first coupling portion 110 when the cap 122 of the second coupling portion 120 is inserted into the insertion hole 116 of the first coupling portion 110.

Since the insertion hole 116 is formed in a circular shape, the cap 122 of the second coupling portion 120 is rotatable in a state in which the cap 122 is inserted into the insertion hole 116. Then, the two head band members 100 are pivotable with respect to each other, and foldable or able to be unfolded when the both ends thereof are coupled to each other. At this time, the two head band members 100 may be unfolded within an angle range of, for instance, 45°, but the concept of the present invention is not limited thereto.

The second coupling portion 120 may include the cap 122 insertable into the insertion hole 116 of the first coupling portion 110 and the flexible ring 124 formed to protrude from a surface of the cap 122. In addition, the flexible ring 124 is accommodated in a circular hole 121 passing through both surfaces of the second coupling portion 120, the flexible ring 124 is connected to an inner circumferential surface of the circular hole 121 through connecting protrusions 126 having a shape protruding from the inner circumferential surface of the circular hole 121.

A surface opposite to a surface where the flexible ring 124 of the cap 122 is formed has a shape having a curved surface rising toward a center thereof. When the cap 122 is inserted into the insertion hole 116, the curved surface is in contact with the inclined surface of the stopper 114 and the coupling protrusion 128, and slides over the inclined surface. Thus, the first coupling portion 110 and the second coupling portion 120 are capable of being smoothly coupled to each other.

The flexible ring 124 is a member which has a ring shape connected to the inner circumferential surface of the circular hole 121 through the connecting protrusions 126, and connects the cap 122 and the inner circumferential surface of the circular hole 121. In addition, the flexible ring 124 may have a ring shape, and have a shape in which the flexible ring 124 is connected with the inner circumferential surface of the circular hole 121 through the connecting protrusions 126 from both ends in a diameter direction.

In addition, the flexible ring 124 includes the coupling protrusion 128 formed to protrude from a position of an outer circumferential surface, and recessed grooves 129 formed in the connecting protrusions 126 in a diameter direction. Then, when the first coupling portion 110 and the second coupling portion 120 are coupled to each other and are pivoted with respect to each other, the coupling protrusion 128 moves over the click protrusion 112. At this time, the flexible ring 124 may be elastically deformed by interference between the click protrusion 112 and the coupling protrusion 128.

Specifically, the flexible ring 124 formed of a flexible material is stretchable and shrinkable in a diameter direction with a more than a certain degree of freedom where the connecting protrusions 126 are not connected to the flexible ring 124. In addition, when the flexible ring 124 shrinks, the recessed grooves 129 formed in the connecting protrusions 126 may become narrower, and stretching or shrinking of the flexible ring 124 becomes comparatively more free, and when the coupling protrusion 128 moves over the click protrusion 112, the flexible ring 124 may shrink in a diameter direction.

The shrunken flexible ring 124 may be restored when the coupling protrusion 128 is accommodated in the coupling groove 118.

In addition, the coupling protrusion 128 may be formed around one of the connecting protrusions 126 formed at both ends in a diameter direction of the flexible ring 124, and when the click protrusion 112 is accommodated in the circular hole 121 and in close contact with one of the connecting protrusion 126, the coupling protrusion 128 may be formed at the position where the coupling groove 118 is positioned.

Thus, when the two head band members 100 forming the head cradle 10 are pivoted with respect to each other, the stopper 114 and the click protrusion 112 are pivoted until in close contact with the connecting protrusion 126 of the second coupling portion 120, and when pivot is completed, the coupling protrusion 128 may be accommodated in the coupling groove 118.

Meanwhile, the strap connection portion 140 may be formed in a shape protruding from the outer circumferential surface of the first coupling portion 110 or the second coupling portion 120. In the embodiment of the present invention, a structure in which the strap connection portion 140 is formed at the first coupling portion 110 is exemplified, but the concept of the present disclosure is not limited thereto.

The strap connection portion 140 is a portion in which the strap 30 connects to mask body 20, and is provided to be able to control the connection with the strap 30 and a length of the strap 30. Hereinafter, a specific structure of the strap connection portion 140 will be described in accordance with accompanying drawings FIGS. 7 to 9.

Figure 7:
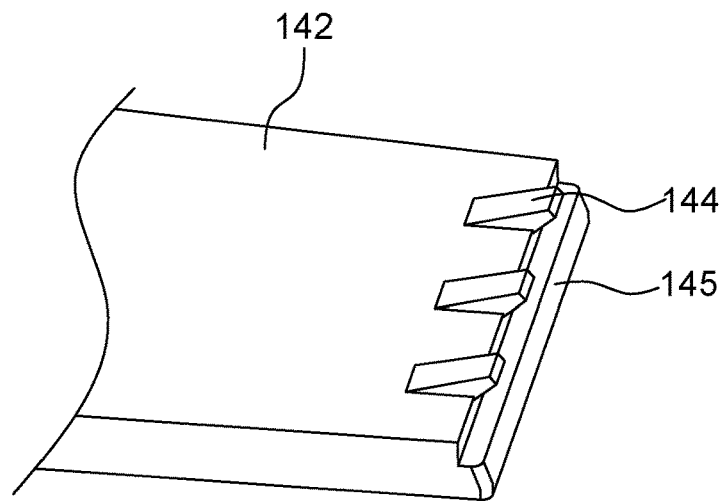
FIG. 7 is a view illustrating the strap grasping protrusion formed on the fixing piece of the strap connection portion in FIG. 1.
Figure 8:
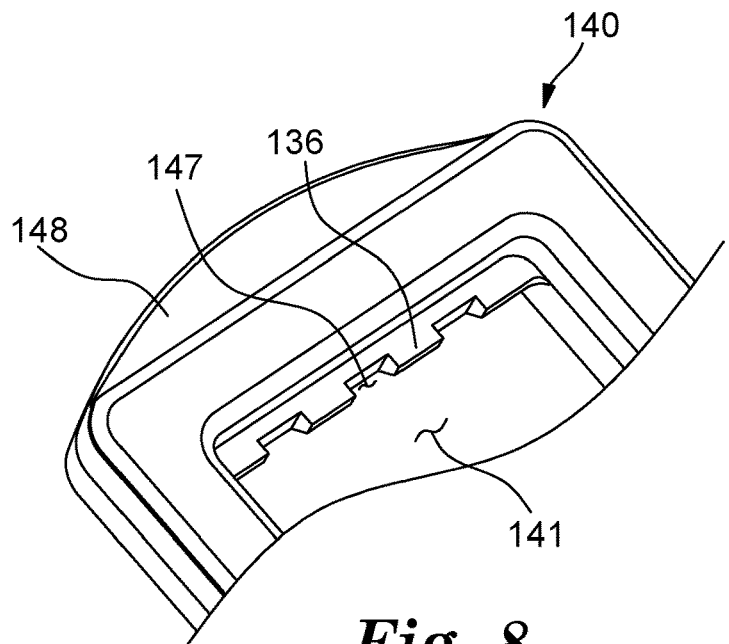
FIG. 8 is a view illustrating an enlarged end portion of the strap connection portion in FIG. 1.
Figure 9:
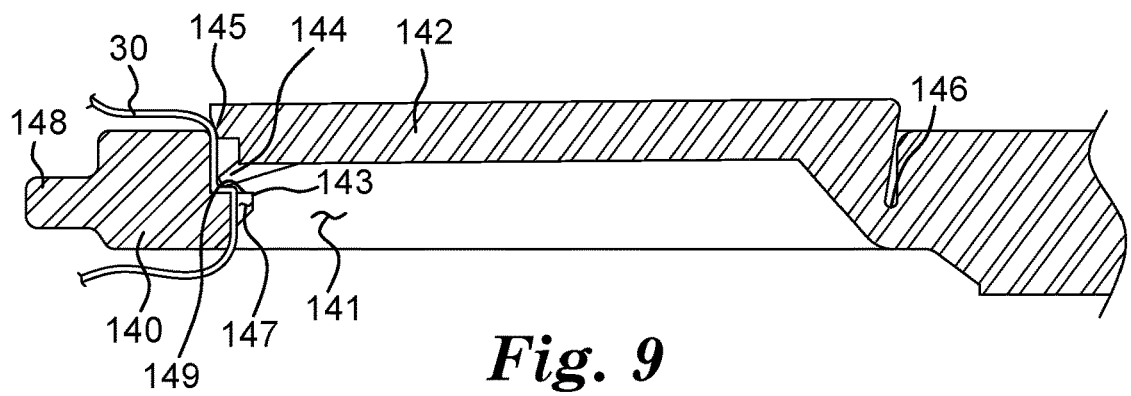
FIG. 9 is a view illustrating a state in which the strap connection portion connected to the strap in FIG. 1 is cut.

FIG. 7 is a view illustrating the strap grasping protrusion formed on the fixing piece of the strap connection portion in FIG. 1, FIG. 8 is a view illustrating an enlarged end portion of the strap connection portion in FIG. 1, and FIG. 9 is a view illustrating a state in which the strap connection portion connected to the strap in FIG. 1 is cut.

Referring to FIGS. 7 to 9, the strap connection portion 140 may include a strap connecting hole 141 having a rectangular shape, and a fixing piece 142 having a rectangular cross-section connected through one side wall forming the strap connecting hole 141 and a hinge 146. In addition, a step portion 143 which selectively engages with an end portion 145 of the fixing piece 142 may be formed to protrude toward an inside of the hole at the other side wall of the strap connecting hole 141.

The fixing piece 142 may be pivoted with respect to the hinge 146 in a state in which the end portion 145 is engaged with a step surface 149 of the step portion 143, and the fixing piece 142 may protrude to an outside of the strap connecting hole 141. Then, the fixing piece 142 may be pivoted to form a gap between the fixing piece 142 and the step portion 143, so that a wearer passes an end portion of the strap 30 through the strap connecting hole 141. In this state, a wearer may push the end portion of the strap 30 into the gap to pass the strap 30 through the strap connecting hole 141, and connect the strap connection portion 140 and the strap 30.

The passed strap 30 may be pinched between the end portion 145 of the fixing piece 142 and the step portion 143, and the position thereof with respect to the head band member 100 may be fixed, and more specifically, the passed strap 30 may be pinched and grasped due to pressure generated when one or more of strap grasping protrusions 144 protruding from the end portion 145 of the fixing piece 142 are inserted into one or more of strap grasping grooves 147 formed in the step portion 143.

To this end, the step portion 143 may include the strap grasping grooves 147 recessively formed from a surface facing an inside of the strap connecting hole 141 at positions corresponding to the strap grasping protrusions 144. In addition, the strap grasping protrusion 144 may be formed at a thickness corresponding to the width of the strap grasping groove 147.

At this time, pressure to grasp the strap 30 may be applied to the strap 30 by the restoring force (torque) generated from the hinge 146 being transmitted to the end portion 145 of the fixing piece 142.

In addition, the strap grasping protrusion 144 may be formed to incline downward at a predetermined angle with respect to a surface of the fixing piece 142 facing the step surface 149 of the step portion 143. Because of this shape, when the strap 30 is grasped, since the pressure to grasp the strap 30 is well transmitted to the strap 30, and the strap 30 is tightly pinched between the strap grasping protrusion 144 and the strap grasping groove 147, a position where the strap 30 is grasped may be well maintained.

In addition, when a wearer controls the length of the strap 30, a passed portion of a part of the strap 30 is pulled in a direction opposite to a protruding direction of the strap grasping protrusion 144 and the strap 30 slides over the inclined surface of the strap grasping protrusion 144, and thus, the length of the strap 30 may be easily controlled in spite of the grasping pressure applied to the strap 30.

At this time, a wearer may easily pull the strap 30 in a state in which an end portion 148 of the strap connection portion 140 is fixed manually.

In addition, when a wearer controls the length of the strap 30 in an opposite direction, the length of the strap 30 may be controlled by pulling the strap 30 in the opposite direction in a state in which the fixing piece 142 is pivoted manually and a gap is formed between the end portion 145 of the fixing piece 142 and the step portion 143.

Hereinafter, the functions and effects of the head band member 100 and the head cradle 10 according to the embodiment of the present invention having the structure described above will be described in accordance with accompanying drawings FIGS. 10 to 12.

Figure 10:
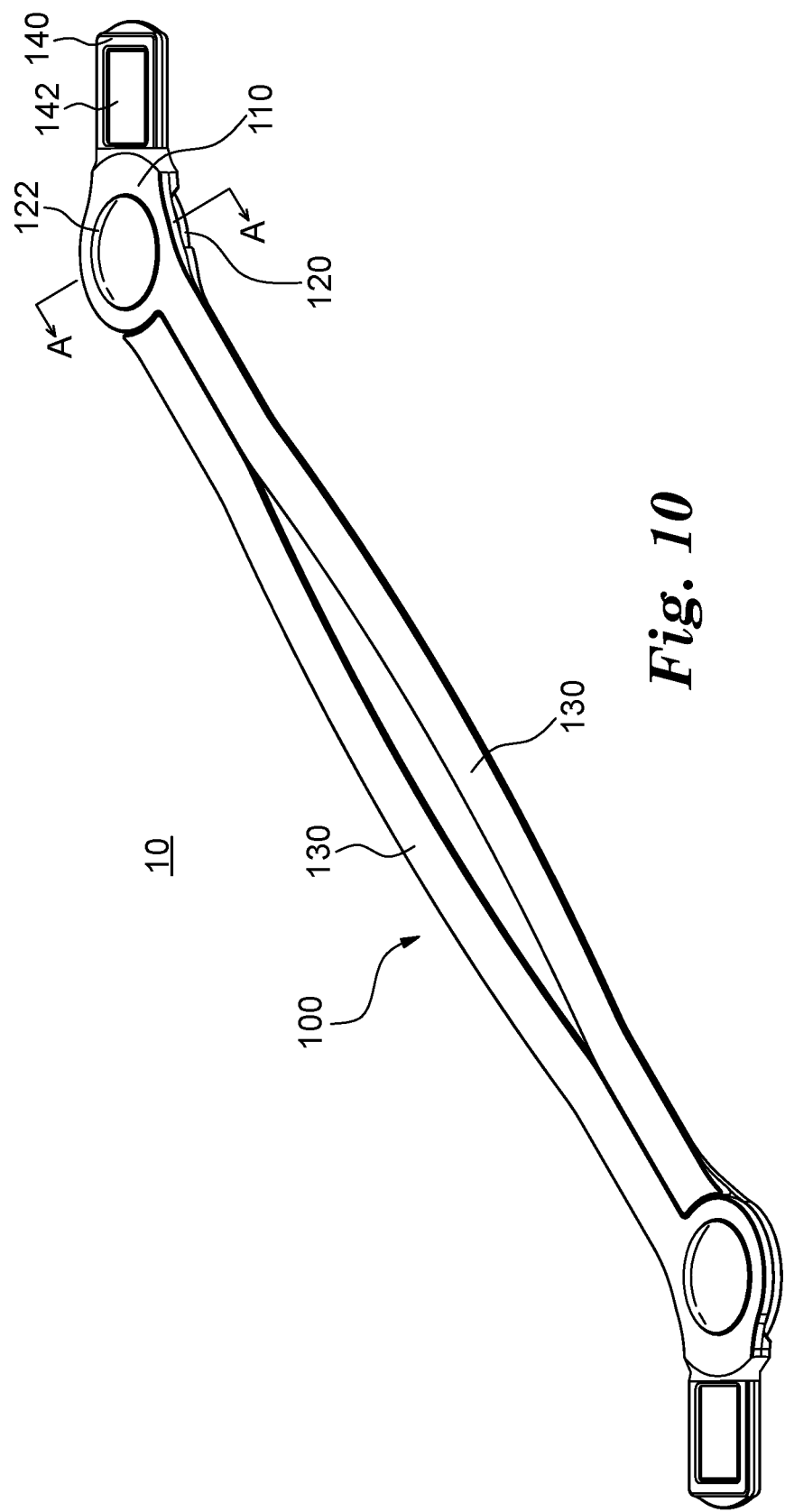
FIG. 10 is a perspective view illustrating a state in which the two head band members in FIG. 1 are coupled to each other and form the head cradle.
Figure 11:
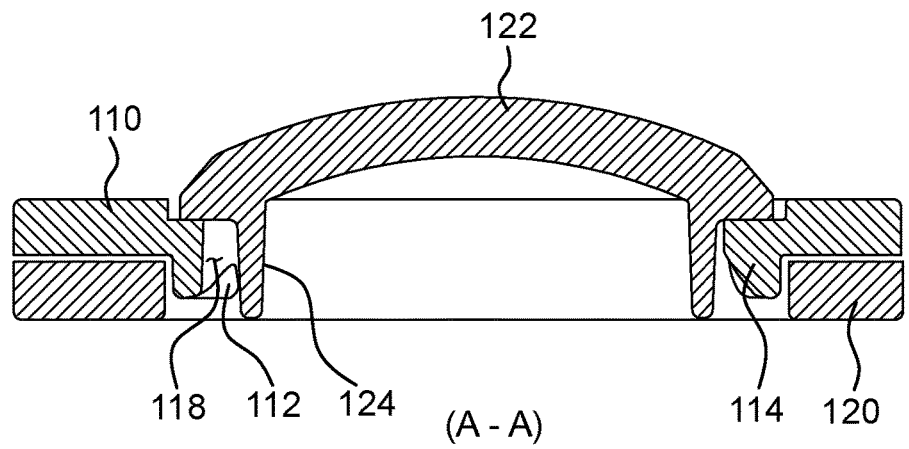
FIG. 11 is a cross-sectional view taken along line A-A of FIG. 10.
Figure 12:
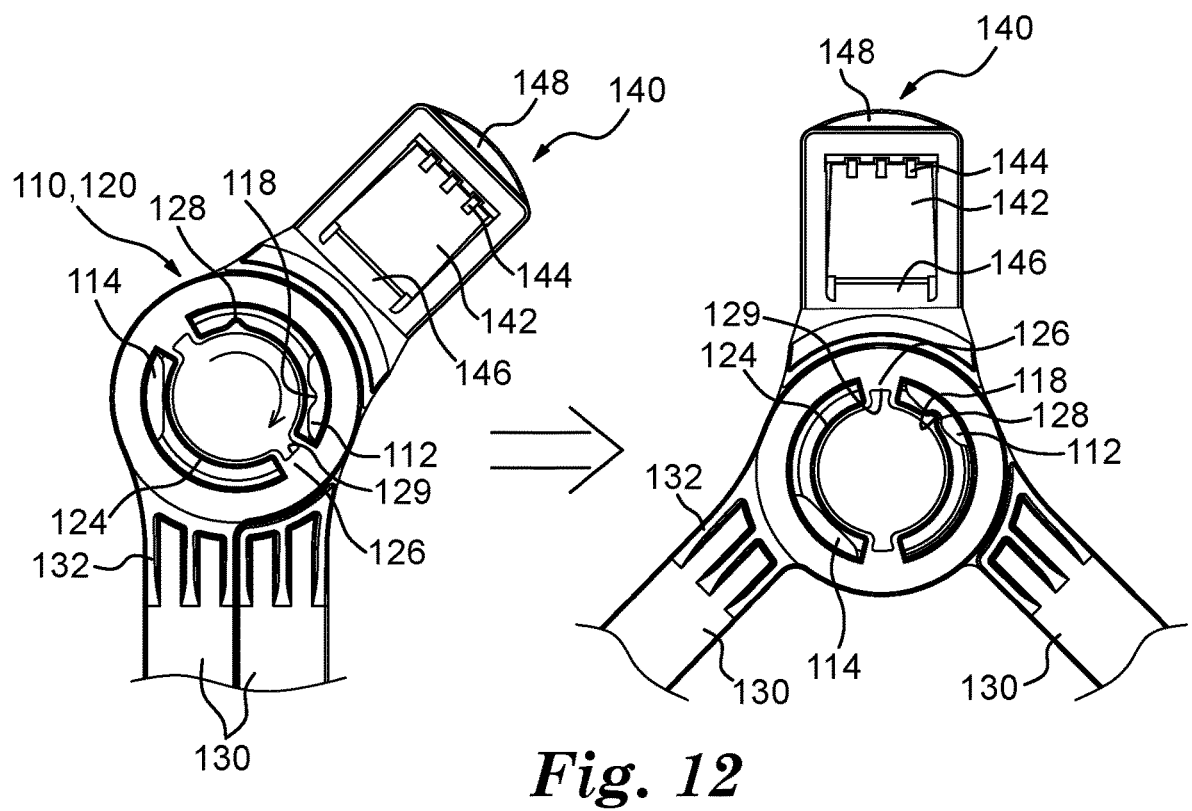
FIG. 12 is a view illustrating a state in which a first coupling portion of one side and a second coupling portion of the other side of the two head band members of the head cradle in FIG. 1 are pivoted with respect to each other in a coupled state.

FIG. 10 is a perspective view illustrating a state in which the two head band members in FIG. 1 are coupled to each other and form the head cradle, FIG. 11 is a cross-sectional view taken along line A-A of FIG. 10, and FIG. 12 is a view illustrating a state in which a first coupling portion of one side and a second coupling portion of the other side of the two head band members of the head cradle in FIG. 1 are pivoted with respect to each other in a coupled state.

Referring to FIGS. 10 to 12, the head cradle 10 according to one embodiment of the present invention is formed by the two head band members 100 being coupled to each other, and at this time, among the two head band members 100, the first coupling portion 110 of one side may be coupled to the second coupling portion 120 of the other side and the first coupling portion 110 of the other side may be coupled to the second coupling portion 120 of one side.

When the first coupling portion 110 and the second coupling portion 120 are coupled to each other, the cap 122 of the second coupling portion 120 may be inserted into the insertion hole 116 of the first coupling portion 110. At this time, when the cap 122 starts to enter the insertion hole 116, a surface of the cap 122 is partially interfered with by the click protrusion 112 and the stopper 114 of the first coupling portion 110, and when force is constantly applied to the cap 122 in an entering direction, a shape of the flexible cap 122 is changed and a surface of the cap 122 in contact with the click protrusion 112 and the stopper 114 slides over the inclined surfaces formed in the click protrusion 112 and the stopper 114.

When the cap 122 is completely inserted through this process, a state in which the cap 122 is caught on the click protrusion 112 and the stopper 114 is maintained, the cap 122 is prevented from escaping in a direction opposite to an insertion direction into the insertion hole 116, and thus, the first coupling portion 110 and the second coupling portion 120 may be completely coupled to each other.

In addition, at least a part of the cap 122 may be accommodated in the insertion hole 116 in a state in which the first coupling portion 110 and the second coupling portion 120 are completely coupled to each other. Thus, when the cap 122 rotates in an inside of the insertion hole 116, the rotation of the cap 122 is guided by the inner circumferential surface of the insertion hole 116.

Hereinafter, a process, in which the head cradle 10 is unfolded or folded by the two head band members 100 coupled to each other through this process being pivoted with respect to each other, will be described.

As illustrated in FIG. 12, in a state in which the cap 122 is accommodated in the insertion hole 116 and the head cradle 10 is folded, a state in which the coupling protrusion 128 of the flexible ring 124 is not accommodated in the coupling groove 118 may be maintained. When the head cradle 10 is unfolded from a folded state, the first coupling portion 110 and the second coupling portion 120 are pivoted with respect to each other and the flexible ring 124 rotates in the inside of the insertion hole 116 of the first coupling portion 110.

When the flexible ring 124 continuously rotates and the coupling protrusion 128 is in contact with the click protrusion 112, the rotation of the flexible ring 124 is interfered with, and at this time, when a torque is continuously applied, the flexible ring 124 is shrunken in a diameter direction, and the coupling protrusion 128 moves over the click protrusion 112, and is accommodated in the coupling groove 118. In this process, while the coupling protrusion 128 moves over the click protrusion 112, the coupling protrusion 128 is suddenly accommodated in the coupling groove 118 and collides with the click protrusion 112, a click sound is generated along with the collision, and a click feeling is conveyed to a wearer.

When the coupling protrusion 128 is accommodated in the coupling groove 118, the stopper 114 and the click protrusion 112 are interfered with by the connecting protrusion 126 of the second coupling portion 120, and the flexible ring 124 is prevented from rotating more.

A wearer may easily unfolded the head cradle 10 through this process, and recognize the completion of unfolding by receiving the conveyed click feeling. In a state in which the head cradle 10 is unfolded, the unfolded state may be maintained by the coupling protrusion 128 being accommodated in the coupling groove 118.

Meanwhile, the strap connection portion 140 may be formed in a twisted manner at a predetermined angle with respect to the supporting member 130, for instance, may be formed twisted by 45°. In this case, when the head cradle 10 is unfolded, the strap connection portion 140 and two supporting members 130 may be unfolded in a symmetrical shape. Specifically, as illustrated in FIG. 12, when the head cradle 10 is unfolded maximally, the two supporting members 130 may be symmetrical with respect to a virtual center line of the strap connection portion 140.

Thus, when the head cradle 10 is worn on the head of a wearer, the strap connection portion 140 may be disposed in a direction toward the mask body 20, and the strap 30 may be disposed to extend toward an extension direction of the strap connection portion 140 and be connected to the mask body 20. Thus, when a wearer controls the length of the strap 30, an effort to align an extension direction of the strap 30 to an extension direction of the strap connection portion 140 is not required.

When the head cradle 10 is folded, the supporting members 130 of the two head band members 100 are maintained in an approximately horizontal state with respect to each other, and while the head cradle 10 is unfolded, central portions of the supporting members 130 move away from each other, and simultaneously, both ends, in which the coupling portions 110 and 120 of the supporting members 130 are positioned, approach each other and the supporting members 130 are bent in a direction. At this time, the supporting members 130 may be induced to only bend in a certain direction, this is allowed by reinforcing portions 132 formed at the same side surfaces at which the supporting members 130 are connected to the two coupling portions 110 and 120.

Specifically, the reinforcing portions 132 are formed at positions in which the first and second coupling portions 110 and 120 and the supporting members 130 are connected to each other, and formed to have a shape in which the thickness thereof decreases from the first and second coupling portions 110 and 120 toward the supporting members 130. In addition, the reinforcing portion 132 may be formed on a surface opposite to a surface from which the cap 122 protrudes. Thus, when the head cradle 10 is unfolded, the head band members 100 may be bent so that the surfaces on which the reinforcing portions 132 are formed face each other, and the head cradle 10 may be unfolded so that the protrusion direction of the cap 122 faces an outside thereof.

The head cradle 10, which is unfolded through this process, may be worn on the head of a wearer in a state in which the head cradle 10 is connected to the mask body 20 through the strap 30, and the mask body 20 may be maintained to be fixed on the face of the wearer.

Meanwhile, a wearer may fold the head cradle 10 to put the respirator mask 1 around the neck thereof. In this case, the wearer may fold the head cradle by pivot them in a direction opposite to a direction in which the two head band members 100 are unfolded. At this time, the coupling protrusion 128 which was accommodated in the coupling groove 118 may again move over the click protrusion 112, and convey a click feeling to the wearer.

According to the head band member 100 and the head cradle 10 of the embodiment of the present invention described above, since the head cradle 10 may be formed by coupling the two head band members 100, which have the same shape, to each other, the manufacturing process is simpler than that of a conventional head cradle including two members having different shapes, and when the mask body 20 is worn on a face, the supporting members 130 are bent at a predetermined angle in a state in which the head cradle 10 is unfolded, and thus, there is an effect in which a feeling that the head cradle 10 is reliably fixed on the head of a wearer may be conveyed to the wearer.

In addition, when the head cradle 10 is unfolded or folded so that the mask is worn on a head or is put around a neck, since a smooth click feeling is conveyed due to an interaction between the click protrusion 112 and the coupling protrusion 128, a problem, in which a conventional head cradle conveys a rattling feeling to a wearer and has difficulty in providing a smooth click feeling to the wearer, may be overcome.

In addition, even when the two head band members 100 are once coupled to each other and repeatedly used for a long time by being folded or unfolded, since a state in which the cap 122 is caught on the stopper 114 and the click protrusion 112 is maintained in a state in which the cap 122 is accommodated in the insertion hole 116, the cap 122 is not easily separated, and thus, there is an effect that the lifetime of products may be increased compared to that of conventional ones.

Meanwhile, there may be cases in which a respirator mask 1 and a helmet are simultaneously worn, for instance, a dangerous work place. In this case, according to the embodiment of the present invention, since the strap 30 is directly connected to the head cradle 10, a wearer should wear the head cradle 10 on the head and wear the helmet by putting the helmet over the head cradle 10. Thus, since the head cradle 10 and the helmet are worn in an overlapped manner, the head of a wearer is pressed more than necessary, and thus, the wearer feels discomfort. In addition, since a helmet is not in close contact with the head of the wearer, when a shock is applied to the head, there may be a problem that the shock may be not properly absorbed.

To solve the above-described problems, a second embodiment of the present invention which will be described is disclosed. Hereinafter, a head band member and a head cradle having the same according to the second embodiment of the present invention will be described in accordance with accompanying drawings FIGS. 13 and 14.

Figure 13A:
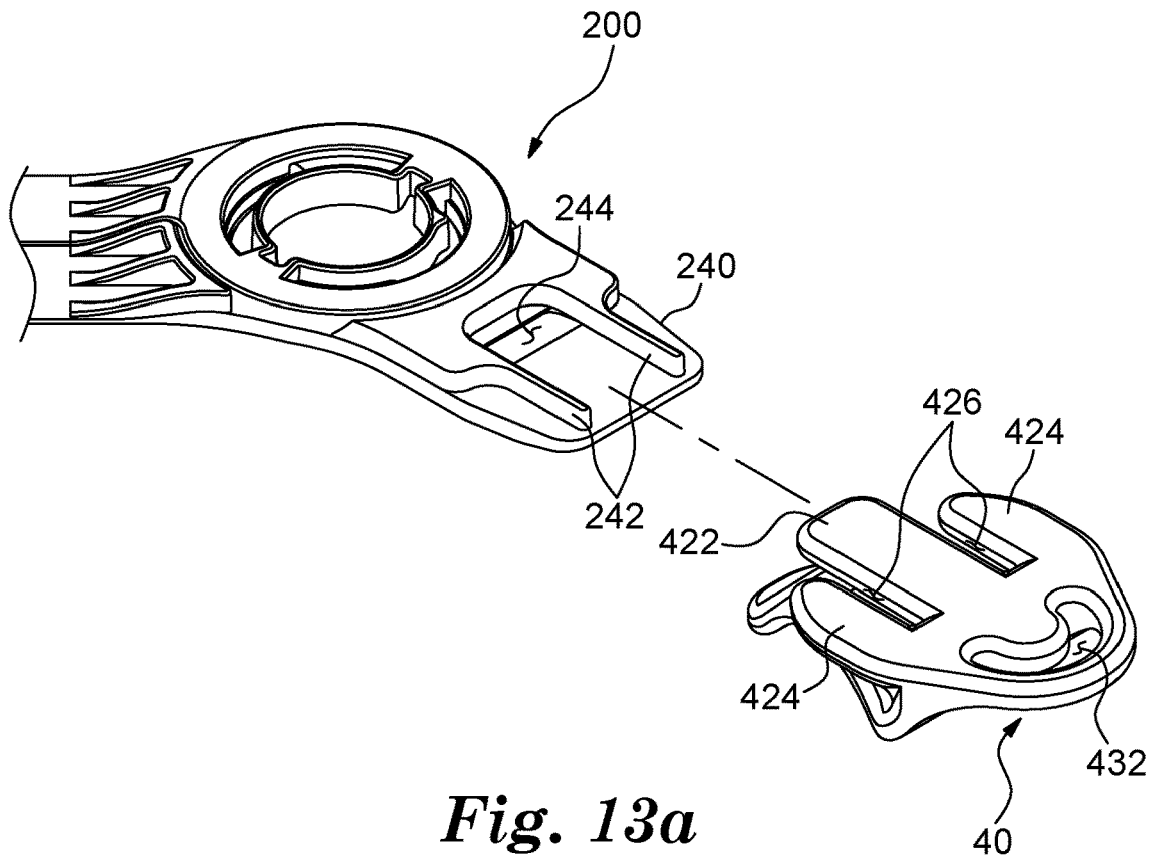
FIG. 13 is a view illustrating a state in which a head cradle according to a second embodiment of the present invention is coupled to a buckle for connecting a strap.
Figure 13B:
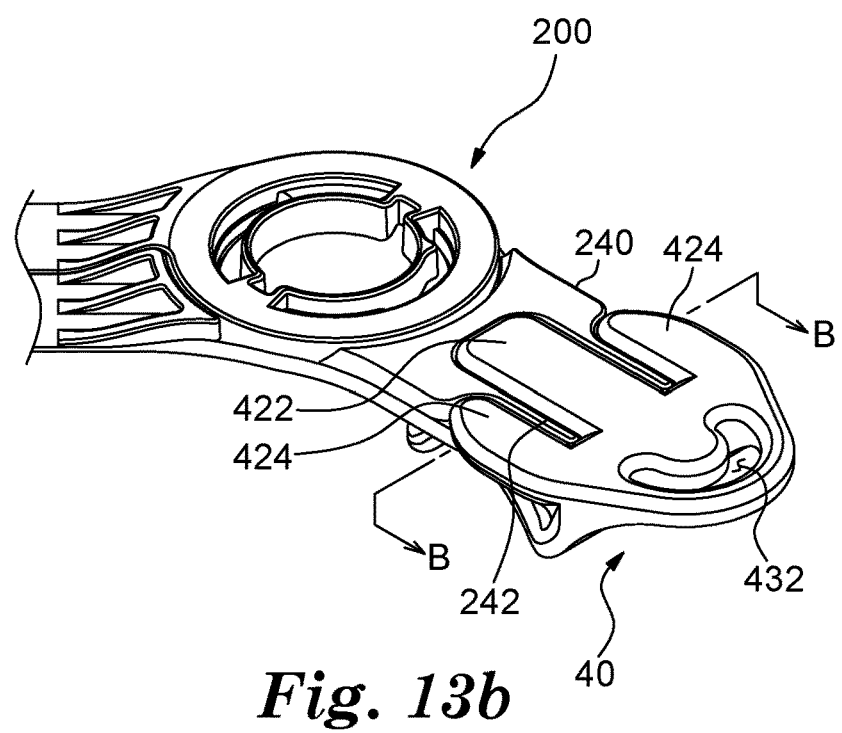
Figure 14:
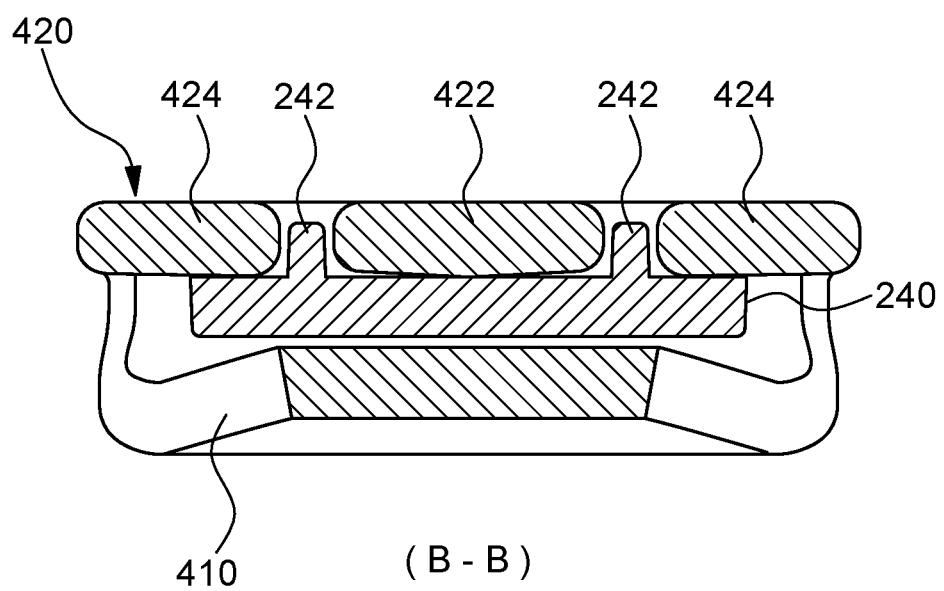
FIG. 14 is a cross-sectional view taken along line B-B of FIG. 13.

FIG. 13 is a view illustrating a state in which a head cradle according to a second embodiment of the present invention is coupled to a buckle for connecting a strap, and FIG. 14 is a cross-sectional view taken along line B-B of FIG. 13.

Referring to FIGS. 13 and 14, a head band member 200 according to another embodiment of the present invention may have a structure in which a strap connection portion 240 has a shape different from that of the embodiment described above, and is connected to a strap 30 through a buckle 40 additionally provided. Hereinafter, the differences described above will be mainly described, and the same descriptions and numerals will be cited from the embodiment described above.

A head cradle 10 formed of head band members 200 according to the embodiment of the present invention may be in close contact with the head of a wearer and maintain a mask body 20, which is connected through the buckle 40 and the strap 30, in close contact with the face of the wearer.

To this end, the strap connection portion 240 has a structure which may be coupled to the buckle 40. Specifically, the strap connection portion 240 may include protruding members 242 which protrude from a surface thereof in a shape and at a position corresponding to coupling grooves 426 of the buckle 40. At this time, the protruding members 242 may be formed to have the same thickness as the width of the coupling grooves 426 in an extension direction from the surface of the strap connection portion 240.

For example, two protruding members 242 may be formed corresponding to two coupling grooves 426 formed in a coupling portion 420 of the buckle 40, a central coupling member 422 of the coupling portion 420 may be inserted into a space between the two protruding members 242. That is, when the buckle 40 is coupled to the coupling portion 420, a position of the buckle 40 with respect to the strap connection portion 240 may be fixed by the protruding member 242 inserted into the coupling groove 426.

In addition, an engaging hole 244, which may accommodate an engaging protrusion (not shown) formed to protrude from a bottom surface of the central coupling member 422 when the buckle 40 is coupled, may be formed in the strap connection portion 240.

A process in which the strap connection portion 240 is coupled to the buckle 40 will be described as follows. In a state in which the buckle 40 is grasped by a wearer, when the buckle 40 approaches the strap connection portion 240, the engaging protrusion of the buckle 40 starts to move forward in a state in which the engaging protrusion of the buckle 40 is in contact with a surface of the strap connection portion 240, an opening of the buckle 40 is widened due to the flexibility of the buckle 40, and the central coupling member 422 may enter a space between the protruding members 242.

When the buckle 40 continuously moves toward the strap connection portion 240 and the engaging protrusion is accommodated in the engaging hole 244, an engaging portion 410 of the buckle 40, which was bent in a manner in which the opening of the buckle 40 was opened, is restored and the engaging protrusion is caught on a side wall forming the engaging hole 244. In other words, the engaging protrusion is accommodated in the engaging hole 244, and an inner wall of the engaging protrusion is in contact with the side wall of the engaging hole 244.

Thus, a process, in which the buckle 40 is coupled to the strap connection portion 240, may be completed, the protruding member 242 is accommodated in the coupling groove 426, and simultaneously, the engaging protrusion is accommodated in the engaging hole 244. Thus, a coupled state between the buckle 40 and the strap connection portion 240 may be maintained.

As described above, since a coupling is allowed even when a wearer simply moves the buckle 40 toward the strap connection portion 240, it allows the mask body 20 to be worn on a face by easily coupling the buckle 40 even in a state in which the strap connection portion 240 is worn on a head.

In addition, when the head cradle 10 is released from coupling with the buckle 40 so that the head cradle 10 is taken off, the engaging portion 410 is pulled to artificially widen the opening of the buckle 40, and the buckle 40 moves forward in a direction opposite to a direction in which the buckle 40 is coupled. Thus, the buckle 40 is easily released. Thus, when a wearer wishes to replace the head cradle 10 with the helmet in a state the wearer wears the head cradle 10, since the head cradle 10 may be taken off by the buckle 40 being released in advance and the mask body 20 may be connected to the helmet by the helmet being worn on the head and the buckle 40 being again coupled to the helmet, there is an advantage that the head cradle 10 is easily replaceable with the helmet.

The following description relates to embodiments of the present invention

An item 1 is a head band member, including a supporting member extending in a direction; a first coupling portion formed at one end portion of the supporting member, and including an insertion hole formed to pass therethrough; a second coupling portion formed at the other end portion of the supporting member; and a strap connection portion formed at an end portion of the first coupling portion or the second coupling portion, and connected with a strap, wherein at least a part of the second coupling portion is inserted into the insertion hole of the first coupling portion and thereby the first coupling portion and the second coupling portion are provided to be coupled to each other, and the head band member is connected to a mask body of a respirator mask through the strap, and a wearing state of the respirator mask is maintained.

An item 2 is the head band member in which the first coupling portion includes a click protrusion formed to protrude from an inner circumferential surface of the insertion hole.

An item 3 is the head band member in which the second coupling portion includes a cap having a shape insertable into the insertion hole; and a flexible ring formed to protrude from a surface of the cap, accommodated in a circular hole formed to pass through the second coupling portion, and connected with an inner circumferential surface of the circular hole through a connecting protrusion protruding from the inner circumferential surface of the circular hole.

An item 4 is the head band member in which the cap is formed in a curved shape in which a surface opposite to a surface on which the flexible ring is formed rises toward a center.

An item 5 is the head band member in which the flexible ring includes a coupling protrusion formed to protrude from a position of an outer circumferential surface of the flexible ring, and a coupling groove in which the coupling protrusion is accommodable is formed in the click protrusion.

An item 6 is the head band member in which the flexible ring includes a recessed groove formed in the connecting protrusion in a diameter direction.

An item 7 is the head band member in which the first coupling portion further includes a stopper formed to protrude from an inner circumferential surface opposite to the click protrusion in a diameter direction.

An item 8 is the head band member in which the strap connection portion includes a fixing piece connected with a side wall of the strap connecting hole, and a step portion to which an end portion of the fixing piece is selectively engaged is protrusively formed on the other side wall of the strap connecting hole.

An item 9 is the head band member in which one or more strap grasping grooves are recessively formed in the step portion of the strap connection portion, and the fixing piece includes a strap grasping protrusion formed to protrude from a surface facing the step surface at a position corresponding to the strap grasping groove.

An item 10 is the head band member in which the strap grasping protrusion is obliquely formed with respect to a surface facing the step surface of the fixing piece.

An item 11 is the head band member in which the strap connection portion is formed in a twisted manner at a predetermined angle with respect to an extension direction of the supporting member.

An item 12 is the head band member in which the strap connection portion is connected to the strap through a buckle having a side connected to the strap.

An item 13 is the head band member in which the strap connection portion includes a surface from which a protruding member protrudes, a coupling groove having a shape corresponding to a shape of the protruding member is formed in the buckle, and the protruding member is inserted into the coupling groove and thereby the strap connection portion is coupled to the buckle.

An item 14 is a head cradle including two head band members coupled to each other, in which the head band member includes a band portion extending in a direction; a first coupling portion formed at one end portion of the band portion, and having an insertion hole formed to pass therethrough; a second coupling portion formed at the other end portion of the band portion; and a strap connection portion formed at an end portion of the first coupling portion or the second coupling portion, and connected with a strap connected with a mask body, wherein, in the two head band members, at least a part of the second coupling portion of one side is inserted into and coupled to the insertion hole of the first coupling portion of the other side, at least a part of the second coupling portion of the other side is inserted into and coupled to the insertion hole of the first coupling portion of the one side, and the two head band member are provided to be pivotable with respect to each other around a center of the first coupling portion and the second coupling portion at a predetermined angle and to be able to unfold or be foldable again from a unfolded state.

An item 15 is the head cradle in which the first coupling portion includes a click protrusion formed to protrude from an inner circumferential surface of the insertion hole.

An item 16 is the head cradle in which the second coupling portion includes a cap having a shape insertable into the insertion hole; and a flexible ring formed to protrude from a surface of the cap, accommodated in a circular hole formed to pass through the second coupling portion, and connected to an inner circumferential surface of the circular hole through a connecting protrusion protruding from the inner circumferential surface of the circular hole, wherein the cap is inserted into the insertion hole and thereby the first coupling portion and the second coupling portion are coupled to each other.

An item 17 is the head cradle in which, when the cap is inserted into the insertion hole, at least a part of the cap is positioned inside the insertion hole, and when the second coupling portion rotates with respect to the first coupling portion, the cap is guided by the insertion hole to rotate.

An item 18 is the head cradle in which the first coupling portion further includes a stopper formed to protrude from an inner circumferential surface opposite to the click protrusion in a diameter direction, wherein the cap is formed in a curved shape in which a surface opposite to a surface in which the flexible ring is formed rises toward a center, and the click protrusion and the stopper include inclined surfaces over which the second surface moves when the cap is inserted into the insertion hole.

An item 19 is the head cradle in which, when the cap is inserted into the insertion hole, the cap is prevented from being separated in a direction opposite to an insertion direction by the click protrusion and the stopper.

An item 20 is the head cradle in which the flexible ring includes a coupling protrusion formed to protrude from a position of an outer circumferential surface of the flexible ring, a coupling groove in which the coupling protrusion is accommodable is formed in the click protrusion, and a recessed groove is formed in the connecting protrusion in a diameter direction.

An item 21 is the head cradle in which the strap connection portion includes a fixing piece connected to a side wall of the strap connecting hole, wherein a step portion to which an end portion of the fixing piece is selectively engaged is protrusively formed on the other side wall of the strap connecting hole.

An item 22 is the head cradle in which one or more strap grasping grooves are recessively formed in the step portion of the strap connection portion, and the fixing piece includes a strap grasping protrusion formed to protrude from a surface facing the step surface at a position corresponding to the strap grasping groove.

An item 23 is the head cradle in which the strap grasping protrusion is obliquely formed with respect to a surface facing the step surface of the fixing piece.

An item 24 is the head cradle in which the strap connection portion is formed in a twisted manner at a predetermined angle with respect to an extension direction of the supporting member, and when the head cradle is unfolded maximally, two supporting members coupled to each other are symmetrized with respect to a virtual central line of the strap connection portion.

An item 25 is the head cradle in which the strap connection portion is connected to the strap through a buckle having a side connected to the strap.

An item 26 is the head cradle in which the strap connection portion includes a surface from which a protruding member protrudes, and a coupling groove having a shape corresponding to a shape of the protruding member is formed in the buckle, and the protruding member is inserted into the coupling groove and thereby the buckle is coupled to the strap connection portion.

Specific embodiments of the head band member for wearing the respirator mask and the head cradle including the same according to the present disclosure have been described merely as examples, but the present disclosure is not limited thereto, and is to be interpreted to have the broadest scope in accordance with the basic idea disclosed in the specification. Those skilled in the art may implement the present invention by combining or replacing these embodiments with patterns of shapes that are not included the disclosed embodiments without departing from the scope of the present disclosure. In addition, those skilled in the art can easily change or modify the disclosed embodiments based on the specification, and it is apparent that such changes or modifications are also included in the scope of the present disclosure.

What is claimed is:

1. A head cradle comprising:
    a first head band member and a second head band member, each head band member comprising:
        a supporting member extending in a direction;
        a first coupling portion formed at one end portion of the supporting member, and including an insertion hole formed to pass therethrough;
        a second coupling portion formed at another end portion of the supporting member; and
        a strap connection portion formed at an end portion of the first coupling portion or the second coupling portion, wherein the strap connection portion is formed at the same end of each head band member,
    wherein at least a part of the second coupling portion of the first head band member is inserted into the insertion hole of the first coupling portion of the second head band member and at least a portion of the second coupling portion of the second head band member is inserted into and coupled to the insertion hole of the first coupling portion of the first head band member, and thereby the first coupling portion of each head band member and the second coupling portion of each head band member are provided to be coupled to each other, and the head cradle is configured to be connected to a mask body of a respirator mask through a strap coupled to each of the strap connection portions to maintain a wearing state of the respirator mask.

2. The head cradle of claim 1, wherein the first coupling portion includes a click protrusion formed to protrude from an inner circumferential surface of the insertion hole.

3. The head cradle of claim 2, wherein the second coupling portion includes:
a cap having a shape insertable into the insertion hole; and
a flexible ring formed to protrude from a surface of the cap, accommodated in a circular hole formed to pass through the second coupling portion, and connected with an inner circumferential surface of the circular hole through a connecting protrusion protruding from the inner circumferential surface of the circular hole.

4. The head cradle of claim 3, wherein the cap is formed in a curved shape in which a surface opposite to a surface on which the flexible ring is formed rises toward a center.

5. The cradle of claim 3, wherein the flexible ring includes a coupling protrusion formed to protrude from a position of an outer circumferential surface of the flexible ring, and a coupling groove in which the coupling protrusion is accommodable in the click protrusion.

6. The head cradle of claim 3, wherein the flexible ring includes a recessed groove formed in the connecting protrusion in a diameter direction.

7. The head cradle of claim 2, wherein the first coupling portion further includes a stopper formed to protrude from the inner circumferential surface opposite to the click protrusion in a diameter direction.

8. The head cradle of claim 1, wherein the strap connection portion includes a fixing piece connected with a side wall of a strap connecting hole, and a step portion to which an end portion of the fixing piece is selectively engaged is protrusively formed on the other side wall of the strap connecting hole.

9. The head cradle of claim 8, wherein one or more strap grasping grooves are recessively formed in the step portion of the strap connection portion, and the fixing piece includes a strap grasping protrusion formed to protrude from a surface facing the step surface at a position corresponding to the strap grasping groove.

10. The head cradle of claim 9, wherein the strap grasping protrusion is obliquely formed with respect to a surface facing the step surface of the fixing piece.

11. The head cradle of claim 1, wherein the strap connection portion is formed in a twisted manner at a predetermined angle with respect to the direction of the supporting member.

12. The head cradle of claim 1, wherein the strap connection portion is connected to the strap through a buckle having a side connected to the strap.

13. The head cradle of claim 12, wherein the strap connection portion includes a surface from which a protruding member protrudes, a coupling groove having a shape corresponding to a shape of the protruding member is formed in the buckle, and the protruding member is inserted into the coupling groove and thereby the strap connection portion is coupled to the buckle.

14. A mask assembly comprising:
a head cradle comprising a first head band member and a second head band member coupled to each other, wherein each head band member includes:
a band portion extending in a direction;
a first coupling portion formed at one end portion of the band portion, and having an insertion hole formed to pass therethrough;
a second coupling portion formed at another end portion of the band portion; and
a strap connection portion formed at an end portion of the first coupling portion or the second coupling portion, wherein the strap connection portion is formed at the same end of each head band member,
wherein, in the two head band members, at least a part of the second coupling portion of the first head band member is inserted into and coupled to the insertion hole of the first coupling portion of the second head band member, at least a part of the second coupling portion of the second head band member is inserted into and coupled to the insertion hole of the first coupling portion of the one first head band member, and the two head band members are provided to be pivotable with respect to each other around a center of the first coupling portion and the second coupling portion at a predetermined angle and to be able to unfold or be foldable again from an unfolded state;
a mask body;
a first strap coupled to the mask body and the strap connection portion of the first head band member; and
a second strap coupled to the mask body and the strap connection portion of the second head band member.

15. The mask assembly of claim 14, wherein the first coupling portion includes a click protrusion formed to protrude from an inner circumferential surface of the insertion hole.

16. The mask assembly of claim 15, wherein the second coupling portion includes:
a cap having a shape insertable into the insertion hole; and
a flexible ring formed to protrude from a surface of the cap, accommodated in a circular hole formed to pass through the second coupling portion, and connected to an inner circumferential surface of the circular hole through a connecting protrusion protruding from the inner circumferential surface of the circular hole,
wherein the cap is inserted into the insertion hole and thereby the first coupling portion and the second coupling portion are coupled to each other.

17. The mask assembly of claim 16, wherein, when the cap is inserted into the insertion hole, at least a part of the cap is positioned inside the insertion hole, and when the second coupling portion rotates with respect to the first coupling portion, the cap is guided by the insertion hole to rotate.

18. The mask assembly of claim 16, wherein the first coupling portion further includes a stopper formed to protrude from an inner circumferential surface opposite to the click protrusion in a diameter direction,
wherein the cap is formed in a curved shape in which a surface opposite to a second surface in which the flexible ring is formed rises toward a center, and the click protrusion and the stopper include inclined surfaces over which the second surface moves when the cap is inserted into the insertion hole.

19. The mask assembly of claim 18, wherein, when the cap is inserted into the insertion hole, the cap is prevented from being separated in a direction opposite to an insertion direction by the click protrusion and the stopper.

20. The mask assembly of claim 16, wherein the flexible ring includes a coupling protrusion formed to protrude from a position of an outer circumferential surface of the flexible ring, a coupling groove in which the coupling protrusion is accommodable is formed in the click protrusion, and a recessed groove is formed in the connecting protrusion in a diameter direction.

* * * * *

UNITED STATES PATENT AND TRADEMARK OFFICE
CERTIFICATE OF CORRECTION

PATENT NO. : 10,716,961 B2  
APPLICATION NO. : 15/752931  
DATED : July 21, 2020  
INVENTOR(S) : Jungchul Moon Page 1 of 1

It is certified that error appears in the above-identified patent and that said Letters Patent is hereby corrected as shown below:

Column 15  
Line 13, in Claim 5, before "cradle" insert --head--.

Column 16  
Line 11, in Claim 14, after "the" delete "one".

Signed and Sealed this  
First Day of September, 2020

Andrei Iancu  
*Director of the United States Patent and Trademark Office*